United States Patent [19]

Giezendanner et al.

[11] Patent Number: 5,073,364

[45] Date of Patent: Dec. 17, 1991

[54] PRESSED POWDER COSMETIC PRODUCT

[75] Inventors: Corinna C. Giezendanner, Wyckoff; Ann Krog, Red Bank, both of N.J.; Nancy Valdes, Baldwin, N.Y.; Joseph DiSomma, Ramsey, N.J.

[73] Assignee: Revlon, Inc., New York, N.Y.

[21] Appl. No.: 540,087

[22] Filed: Jun. 19, 1990

[51] Int. Cl.⁵ .................... A61K 7/02; A61K 7/035
[52] U.S. Cl. ........................... 424/63; 424/69; 132/294; 132/303; 514/844
[58] Field of Search ............ 424/63, 69; 132/294, 132/303; 514/844

[56] References Cited

U.S. PATENT DOCUMENTS 3,978,207 8/1976 Fotiu et al. ...................... 424/63
4,279,890 8/1981 Harris et al. .................... 424/69
4,390,524 6/1983 Nasuno et al. .................. 424/63
4,534,963 8/1985 Gordon ........................... 424/69

FOREIGN PATENT DOCUMENTS 120182 1/1986 Japan .

Primary Examiner—Thurman Page
Assistant Examiner—Amy Hulina
Attorney, Agent, or Firm—Julie Blackburn

[57] ABSTRACT

A pressed powder cosmetic product is disclosed. The product, useful as an eyeshadow, a blusher and the like, comprises a cream pressed powder composition and a frost pressed powder composition disposed adjacent to each other in the same pan. This unique arrangement is made possible by inclusion of surfactant coated fillers, surfactant coated colorants and a two component powder binder constituent.

19 Claims, No Drawings

PRESSED POWDER COSMETIC PRODUCT

BACKGROUND OF THE DISCLOSURE

1. Field of the Invention

Pressed power products are an important class of cosmetics which find application in a plurality of cosmetic uses. Such very important cosmetic products as eyeshadow, eyeliner, blush, cake mascara, face powder and the like are packaged exclusively or alternatively as pressed powders. Many of these pressed powder products come in matte and high luster finishes. In many cases it is desirable to include both types of powders in a single product package in order to maximize beauty enhancement of the cosmetic product. For instance, eyeshadow products oftentimes includes at least two pans, one which holds at least one matte or "cream" shade and the other at least one high luster or "frost" shade.

A major problem associated with the production of pressed powder cosmetic products in the prior art has been the inability to dispose cream and frost pressed powder compositions in the same pan, tray or container. This inability is due to the fact that pressed powders are formed by the imposition of pressure which transforms loose powder compositions into pressed powder compositions. Since powder in a single pan, the term used for a container in the cosmetic arts, is formed into a unitary solid by the imposition of a fixed pressure, cream and frost pressed power compositions, which have different constituencies, could not be disposed in the same pan. This was because a single pressure could not be used to successfully compact cream and frost pressed powder compositions.

This problem, which prevents the manufacture of pressed powder cosmetic products in which cream and frost pressed powders are disposed in the same pan, represents a major marketing failing. The placing of both cream and frost pressed powder compositions in the same cosmetic pan is not only more attractive to consumers but better displays the advantages to be obtained by the user than is obtained by the disposition of the two compositions in separate pans. By placing cream and frost pressed powder compositions adjacent to each other, the user is better informed of the advantages to be obtained by applying the two classes of pressed powder composition to the skin, especially the face, to provide maximum beauty enhancement.

Another area of continual research in the pressed powder cosmetic product arts is the devlopment of products providing improved moisturization, emolliency and smoothness. These properties are oftentimes sacrificed in order to enhance the beautifying effects of these cosmetics. Clearly, a new class of pressed powder cosmetic products which provide these beneficial effects to the user's skin without sacrificing beauty enhancement is much desired in the art.

2. Background of the Prior Art

The problems associated with the production of cosmetic pressed powders have been addressed in the prior art. U.S. Pat. No. 4,609,545 to Schlossman describes the addition of a compressing aid, added to a powdery composition, to provide a pressed powder cosmetic product characterized by good compressibility, low dusting, sufficient powder release without glazing, good adhesion, smooth surface, the absence of crumbling and a strong cake.

The compressing additive of the '545 patent is a synthetically prepared saturated hydrocarbon wax, having an average molecular formula of $C_{48}H_{98}$, an average molecular mass of 700 and a congealing point of about 204° F. The wax is sometimes coated with low viscosity esters of fatty acids or alcohols such as isopropyl myristate, lauryl acetate or ethylhexyl palmitate. Alternatively, the wax particles can be coated with a silicone fluid such as dimethylpolysiloxane, having the CTFA name dimethicone. Alternatively, instead of a lubricant, the surface of the wax can be coated with zein, a protein of corn gluten. These coatings are employed to improve the dispersal of the wax particles with pressed powder compounds. However, these coatings increase the pressure required to compress the powdery composition.

U.S. Pat. No. 4,622,074 to Miyoshi et al. teaches the coating of pigments or extender pigments, i.e., fillers, with hydrogenated lecithin or the reaction product of hydrogenated lecithin and a metal salt. The cosmetic composition, albeit, not a pressed powder, containing such coated pigments or coated extender pigments is said to provide excellent protection for the skin, resistance to wear and good water repellency.

The above brief description of representative references relevant to the present invention indicates that coatings for powders are known in the art. It also establishes that additives specially included in pressed powder compositions to improve their compressibility are also known in the art. However, the above discussion emphasizes the absence in the art of a teaching directed to a pressed powder cosmetic composition which overcomes the earlier discussed problems associated with production of frost and cream pressed powder compositions in a single pan to meet this well established need in this art.

BRIEF SUMMARY OF THE INVENTION

A new class of cosmetic composition, which permits the production of a pressed powder cosmetic product, has now been discovered. This new pressed powder cosmetic product provides at least one cream and one frost pressed powder composition in the same pan to enhance presentation attractiveness. This beneficial packaging advantage, surprisingly, occurs without lessening the effectiveness of the cosmetic properties of the pressed powder compositions. Indeed, the cream and frost pressed powder compositions of this product represents an advance in pressed powder technology providing improved emolliency, moisturization and smoothness compared to the pressed powder cosmetic products of the prior art.

In accordance with the present invention, a pressed powder cosmetic product is provided. This cosmetic product includes at least one cream pressed powder composition and at least one frost pressed powder composition disposed adjacent to each other in a single pan.

DETAILED DESCRIPTION

The cosmetic product of the present invention comprises a matte finish pressed powder composition, better known in the art as a cream pressed powder composition, disposed adjacent to a high luster pressed powder composition, better known in the art as frost pressed powder composition, in the same pan. This unique product is producible because of the novel nature of the cream and frost pressed powder compositions that together constitute the cosmetic product of the present invention.

The unique cream and frost pressed powder composition is produced by coating at least a portion of the filler and colorant constituents and by employing a novel two component powder binder constituent in both the cream and frost pressed powder compositions. That is, the cream and frost pressed powder compositions of the subject cosmetic product include filler and colorant constituents which are coated and a two component powder binder constituent so that the cream and the frost compositions can be packaged in the same pan without loss of cosmetic functionality.

Those skilled in the cosmetic arts are aware that the processing of cream and frost pressed powder compositions in the same pan was not possible in the prior art due to the inclusion of high concentration in frost pressed powder compositions, but not in cream compositions, of pearlescent powders. This difference in pearlescent powder concentration made the required pressure for solidification of cream and frost pressed powder compositions too divergent for utilization of a single average pressure. In the present invention, the coating of some or all of the filler and colorant constituents of the cream and frost pressed powder compositions in combination with a novel powder binder constituent permit a common pressure to be applied to form the cream and the frost pressed powder compositions of the cosmetic product of the present invention into unitary solids.

Those skilled in the art are furthermore aware that cosmetic pressed powder compositions, cream and frost, are utilized in such cosmetic applications as eyeshadow, blush, face powders, skin foundations and the like. All of these cosmetic products have in common their disposition on the surface of the skin. Therefore, an effective pressed powder composition should impart moisturization, emolliency and smoothness to the surface of the skin upon which it is applied.

It has surprisingly been found that these desirable effects on the skin can be obtained while also, at the same time, permitting the employment of a single pressure to press together cream and frost powder compositions in the same pan. This advance in the art is derived by coating some or all of the filler and colorant constituents of the cream and frost pressed powder compositions with cosmetically acceptable surfactants. Among the surfactants within the contemplation of use in the present cosmetic composition as a filler and cosmetic coating are lecithin, egg oil, egg yolk extract, animal collagen amino acids, animal elastin amino acids, animal keratin amino acids and mixtures thereof. These ingredients are fully defined in the CTFA Cosmetic Ingredient Dictionary, Third Edition, The Cosmetic, Toiletry and Fragrance Association, Washington, D.C. (1982) or in the CTFA Cosmetic Ingredient Dictionary, Third Edition, Supplement (1985). These publications are incorporated herein by references.

Although all of these ingredients serve to provide, along with the unique powder binder constituent, the means for producing the desired results obtained in the cosmetic product of this invention, it is particularly preferred that the coating be provided by lecithin.

The use of a cosmetic acceptable surfactant, especially lecithin, as a coating of filler and colorant constituents is illustrated by the cream pressed powder composition utilized in the cosmetic product of this invention. Fillers within the contemplation of the present invention that may be utilized in the cream pressed powder composition include talc, mica, bentonite, bismuth oxychloride, calcium silicate, calcium carbonate, nylon, polyvinylidene copolymers, isopropyl triisostearyl titanate, corn starch, kaolin and the like. It is again emphasized that these constituents, as well as those to be mentioned hereinafter, encompass classes of materials within the meaning of those ingredients as defined in the aforementioned CTFA Cosmetic Ingredient Dictionary, Third Edition, incorporated herein by reference. It is noted, however, that although polyvinylidene copolymers and isopropyl triisostearyl titanate are cosmetically acceptable and have defined CTFA meanings they are of recent development and are not included in the latest, the Third Edition or its supplement, of the Dictionary. It is believed that these ingredients will be included in the next edition of the Dictionary.

It is emphasized that the cream pressed powder composition is restricted only by the requirement that a fraction of the filler utilized therein be surfactant coated. A fraction, therefore, of the filler constituent of the cream pressed powder composition may be non-coated. In a preferred embodiment, however, all the filler constituent of the cream pressed powder composition of this cosmetic product is surfactant coated, preferably, lecithin coated.

In a preferred embodiment of the present invention, the filler constituent of the cream pressed powder composition, preferably all surfactant coated, constitutes between about 30% and about 90% by weight, based on the total weight of the cream pressed powder composition. More preferably, the surfactant coated filler is representative of between about 50% and about 75% of the cream pressed powder composition. It should be understood that hereinafter all recited percentages of cream pressed powder constituents represent percent by weight, based on the total weight of the cream pressed powder composition.

In one preferred embodiment the surfactant coated filler constituent comprises lecithin coated talc and lecithin coated mica. In this preferred embodiment the lecithin coated talc component is representative of between about 2% and about 50%. More preferably, the lecithin coated composition talc component constitutes between about 20% and about 40% of the cream pressed powder. Preferably, the lecithin coated mica constituent of this preferred cream pressed powder composition comprises between about 5% and about 50%. In a more preferred embodiment, the lecithin coated mica component constitutes between about 15% and about 35% of the cream pressed powder composition.

A second major constituent of the cream pressed powder composition is a colorant. Preferred ingredients, that may be utilized as the colorant constituent in the cream pressed powder composition of the cosmetic product, include titanium dioxide, titanated mica (titanium dioxide on mica), iron oxides, carmine, chromium hydroxide green, chromium oxide greens, ferric ammonium ferrocyanide, ferric ferrocyanide, manganese violet, ultramarine blue, ultramarine blue, ultramarine violet, ultramarine red, ultramarine pink, D&C Red No. 6 barium/strontium lake, D&C Red No. 7 calcium lake, D&C Red No. 27 aluminum lake, D&C Red No. 30 lake, D&C Yellow No. 5 aluminum lake, D&C Yellow No. 6 aluminum lake and mixtures thereof. Again, the colorants recited hereinabove are defined by the aforementioned CTFA Cosmetic Ingredient Dictionary.

It is emphasized, however, that in addition to the preferred colorants enumerated above other colorants certified for use in cosmetic compositions are within the contemplation of the pressed powder composition of the present invention. Indeed, the CTFA certified colorants listed in Section 2 of the CTFA Cosmetic Ingredient Handbook, First Edition, The Cosmetic, Toiletry and Fragrance Assn., Inc., Washington, D.C. (1988) at pp. 62-63, incorporated herein by reference, are all within the contemplation of the colorant component of the cream pressed powder composition of the present invention. This list includes all the preferred colorants mentioned above.

It is emphasized, as in the case of the filler constituent, that only a fraction of the colorant need be surfactant coated. Again, as in the case of the filler, it is preferred that the higher the percent of the colorant surfactant coated, the more effective is its use in the cosmetic product of this invention. Those skilled in the art are aware, however, that water soluble colorants cannot be surfactant coated. As such, when such colorants are employed in the cream pressed powder composition, they are not surfactant coated.

In a preferred embodiment between about 0.1% and about 40% of the cream pressed powder composition is surfactant coated colorant while between about 0.1% and about 30% of that composition is uncoated colorant. More preferably, surfactant coated colorant contributes between about 0.1% and about 15% of the cream pressed powder composition.

In a particularly preferred embodiment the surfactant coated colorant constituent of the cream pressed powder preferably comprises between about 1.0% and about 30% lecithin coated colorant. Similarly it is particularly preferred that the uncoated pigment constituent of the cream pressed powder composition comprise between about 0.10% to about 10% colorant.

A further constituent of the cream pressed powder composition is a powder binder. The powder binder constituent is essential in binding the filler and colorant constituents into a pressed powder composition. This critical constituent is present in the composition in a concentration of between about 0.5% and about 15% by weight. Preferably, the powder binder constituent comprises between about 1% and about 7% of the cream pressed powder composition.

The unique powder binder constituent of the cream pressed powder composition includes two components. A first component is selected from the group consisting of polyethylene, boron nitride, polymethylmethacrylate and mixtures thereof. Of this group of first component ingredients, polyethylene is included in the Monograph Section of aforementioned CTFA Cosmetic Ingredient Dictionary, Third Edition, incorporated herein by reference. Boron nitride and polymethylmethacrylate are CTFA approved cosmetic ingredients not yet listed in the Dictionary. The first powder binder component represents at least about 2% by weight of the cream pressed powder composition. Preferably, the first powder binder component represents between about 2% to about 5% of the cream pressed powder composition.

The second powder binder component includes ingredients selected from the group consisting of zinc stearate, calcium stearate, lithium stearate, magnesium stearate, lauroyl lysine, calcium silicate, kaolin and mixtures thereof. All of the above ingredients are mentioned in the CTFA Cosmetic Ingredient Dictionary, Third Ed., incorporated herein by reference, except lauroyl lysine. That ingredient, acceptable for use in cosmetics, will appear in the next edition of the Dictionary. The second powder binder component is present in the cream pressed powder composition in an amount of at least about 1%, preferably in a concentration of between about 1% and about 5% of the total weight of the cream pressed powder composition.

A particularly preferred powder binder constituent is provided by a combination of polyethylene as the first component and zinc stearate as the second component.

Another important constituent of the cream pressed powder composition of the cosmetic product of this invention is generally referred to as the liquid binder. The liquid binder constituent contributes moisturization, emolliency and smoothness to the composition's affect on the user's skin. It is emphasized, in this regard, that the surfactant, especially lecithin, coated on filler and colorant constituents, also contributes significantly in the composition's ability to provide these desirable skin effects.

The liquid binder constituent preferably comprises between about 1% and about 20% by weight, based on the total weight of the cream pressed powder composition. More preferably, the liquid binder constituent comprises between about 5% and about 13% by weight.

The liquid binder constituent, present in these preferred concentration ranges, is made up of esters and silicones. Among the preferred esters and silicones constituting the liquid binder constituent of the cream pressed powder composition are coco-caprylate/caprate, C12-15 alcohols benzoate, octyldodecyl stearoyl stearate, dimethicone, trimethylsiloxysilicate and mixtures thereof. Although other esters and silicones may be utilized in the liquid binder constituent, a mixture of the above recited ingredients, denoted by their CTFA monograph designations, as defined in the CTFA Cosmetic Ingredient Dictionary, Third Edition, incorporated by reference, is preferred.

In the preferred embodiment of the cream pressed powder composition wherein the liquid binder constituent includes the above recited ingredients, coco-caprylate/caprate, an ester, is present in a concentration in the range of between about 0.10% and about 5.0% by weight. More preferably, this constituent is present in a concentration in the range of between about 1.0% and about 3.0%. A second ester, C12-15 alcohols benzoate constitutes between about .10% and about 5.0% by weight, more preferably, between about 1.0% and about 3.0%. Yet a third ester, octyldodecyl stearoyl stearate is included in an amount of between about 0.05% and about 2.0%, more preferably, between about 0.25% and about 1.00% by weight. The silicone component, comprising a mixture of dimethicone and trimethylsiloxysilicate, represents between about 1% and about 7% by weight. More preferably, the mixture of dimethicone and trimethylsiloxysilicate is representative of between about 2% and about 6%.

A final constituent, preferably present in the cream pressed powder composition, is one or more preservatives. Preservatives are utilized to preserve the cosmetic composition during the period between the time it is made and the time it is utilized. A whole host of preservatives, included in the CTFA Cosmetic Ingredient Dictionary, Third Edition, are employable in the cream pressed powder composition. However, methylparaben, ethylparaben, propylparaben and imidazolidinyl urea are particularly preferred for use as the preservative constituent in the cream pressed powder composition.

The preservative constituent of the cream pressed powder composition preferably constitutes between about 0.25% and about 2% by weight, more preferably, between about 0.5% and about 1.5% by weight. In the preferred embodiment wherein the preservative components recited above are utilized, methylparaben, ethylparaben and propylparaben together constitute between about 0.1% and about 1% by weight. More preferably, these components comprise between about 0.2% and about 0.8% by weight. Imidazolidinyl urea, in a preferred embodiment, is provided in the cream pressed powder composition as a coating on talc. The imidazolidinyl urea coated talc is preferably incorporated in an amount of between about 0.2% and about 1% by weight. More preferably, this concentration is between about 0.4% and about 0.8% by weight.

For clarity, it is again emphasized that all of the above recited concentrations are by weight, based on the total weight of the cream pressed powder composition.

Turning to the frost pressed powder composition, which is provided in the same pan as the cream pressed powder composition in the cosmetic product of this invention, it is primarily distinguished from the cream pressed powder composition by the incorporation therein of a considerable higher concentration of pearl colorant constituent. Although pearl colorant may be included, and in a preferred embodiment is included, as a constituent of the cream pressed powder composition, that constituent is included in small concentration in the cream pressed powder composition.

The pearl colorant constituent of the frost pressed powder composition is provided by pearlescent powder. Pearlescent powders within the contemplation of the frost pressed powder composition include uncoated titanated mica, ferric ammonium ferrocyanide coated on titanated mica, manganese violet coated on titanated mica, iron oxides coated on titanated mica, carmine coated on titanated mica, chromium oxide greens coated on titanated mica, chromium hydroxide green coated on titanated mica and mixtures thereof. Although other pearlescent powders may be utilized, the above ingredients are preferred for use in the frost pressed powder composition.

In totality, the pearl colorant constituent preferably comprises between about 20% and about 60% by weight, based on the total weight of the frost pressed powder composition. More preferably, the pearl colorant constituent constitutes between about 25% and about 40% of the frost pressed powder composition. It is emphasized that the above percentages and those recited below, directed to concentrations of constituents of the frost pressed powder composition, are representative of the constituent's percentage by weight, based on the total weight of the frost pressed powder composition.

In addition to the pearl colorant constituent, the frost pressed powder composition includes other colorant constituents including an uncoated colorant. The uncoated colorant constituent is preferably one or more of bismuth oxychloride, carmine, ferric ferrocyanide, D&C Red No. 6 barium/strontium lake, D&C Red No. 7 calcium lake, D&C Red No. 27 aluminum lake, D&C Red No. 30 lake, D&C Yellow No. 5 aluminum lake, D&C Yellow No. 6 aluminum lake and the like. These colorants may be either unsupported or disposed on mica, talc or bismuth oxychloride. The uncoated colorant constituent is representative of between about 0% and about 15% by weight. Preferably, the uncoated colorant constituent provides between about 1% and about 10% by weight of the frost pressed powder composition.

A third colorant constituent included in the frost pressed powder composition is surfactant coated colorant. As in the case of the cream pressed powder composition, the surfactant coating may be any one of lecithin, egg oil, egg yolk extract, animal elastin amino acids, animal keratin amino acids, animal collagen amino acids and the like. As in the case of the surfactant coating colorant of the cream pressed powder composition, lecithin is the preferred surfactant coating.

The preferred colorant itself, which is surfactant coated, is any one or more of iron oxides, chromium hydroxide green, chromium oxide greens, ultramarine blue, ultramarine green, ultramarine pink, ultramarine red, ultramarine violet and the like.

The coated colorant constituent comprises between about 0.1% and about 40% by weight of the frost pressed powder composition. Preferably, the surfactant coated colorant constituent encompasses between about 1% and about 10% by weight of the frost pressed powder composition.

The frost pressed powder composition, like the cream pressed powder composition, is characterized by the incorporation therein of one or more fillers. The filler constituent is preferably surfactant coated. In a preferred embodiment the same surfactant which coats the colorant is used to coat all or a portion of the filler constituent. In that the same surfactant coatings are preferably employed, it follows that the surfactant is preferably one or more lecithin, egg oil, egg yolk extract, animal elastin amino acids, animal keratin amino acids and animal collagen amino acids. As in the surfactant coating of the colorant, lecithin is the most preferred surfactant for use as the filler coating.

The coating or at least a portion of the filler with a surfactant, preferably lecithin. as in the case of the cream pressed powder composition, not only permits processing of the frost and cream pressed powder compositions in the same pan, as discussed above, but in addition, provides the frost pressed powder composition with improved moisturization, emolliency and smoothness It should be appreciated, however, that the frost pressed powder composition may include an uncoated filler constituent which may or may not be the same filler or fillers as the coated filler or fillers.

The frost pressed powder composition is characterized by the incorporation therein of between about 15% and about 50% surfactant coated filler. More preferably, the frost pressed powder composition includes between about 20% and about 35% surfactant coated filler.

The preferred filler ingredients, coated with a surfactant, within the contemplation of the frost pressed powder composition, include talc, mica, bentonite, bismuth oxychloride, calcium silicate, calcium carbonate, nylon, polyvinylidene copolymers, corn starch, isopropyl triisostearyl titanate, kaolin, mixtures thereof and the like. As in the case of the cream pressed powder composition, the preferred surfactant coated fillers are talc, mica and mixtures thereof. Other CTFA cosmetically approved fillers not included in the above preferred grouping are also employable in the frost pressed powder composition.

Although the frost pressed powder composition is preferably surfactant coating, that composition may include uncoated filler. Indeed, in a preferred embodiment the frost pressed powder composition comprises uncoated filler. In the preferred embodiment wherein the frost composition includes uncoated filler, it is present in a concentration of between about 0.1% and about 25%. More preferably, the uncoated filler constituent comprises between about 2% and about 15% of the pressed powder composition.

In the preferred embodiment wherein uncoated filter is present in the frost pressed powder composition it is preferred that it be talc, mica and mixtures thereof. Of these, talc is particularly preferred for use as the uncoated filler.

The frost pressed powder composition includes a powder binder constituent. The powder binder constituent, which serves the same function in the frost pressed powder composition as in the cream pressed powder composition, comprises between about 3% and about 15% of the frost pressed powder composition. More preferably, the powder binder constituent is representative of between about 5% and about 10% of the frost pressed powder composition.

As in the unique cream pressed powder composition, the powder binder constituent of the frost pressed powder composition includes both a first and a second component. Again, the first powder binder component is selected from the group consisting of polyethylene, boron nitride, polymethylmethacrylate and mixtures thereof. Similarly, the second powder binder component is selected form the group consisting of zinc stearate, calcium stearate, lithium stearate, magnesium stearate, lauroyl lysine, calcium silicate, kaolin and mixtures thereof. As in the particularly preferred preferred embodiment of the cream pressed powder composition, the powder binder constituent, most preferably, comprises a combination of polyethylene and zinc stearate as the first and second components, respectively.

Independent of the specific ingredients used as the first and second powder binder components, they are individually present such that the first powder binder component comprises at least 2% by weight of the total weight of the frost pressed powder composition, preferably between about 2% and about 5% by weight of the composition. The second component of the powder binder constituent is present in an amount constituting at least about 1%, preferably between about 1% and about 10% by weight, of the frost pressed powder composition.

Yet another preferred constituent of the frost pressed powder composition is an oil binder. The oil binder constituent, as in the case of the cream pressed powder composition, serves to enhance moisturization, emolliency and smooth feel of the frost pressed powder composition of the cosmetic product of this invention. Thus, it is not surprising that it, like the oil binder constituent of the cream pressed powder composition, comprises esters and silicones. It is noted however, that the oil binder constituent is present in greater concentration in the frost pressed powder composition than in the cream pressed powder composition of the cosmetic product of this invention. The oil binder constituent of the frost pressed powder composition is preferably between about 7% and about 22%. More preferably, the oil binder comprises between about 10% and about 20% of the frost pressed powder composition.

In a preferred embodiment, the ester components of the oil binder constituent include coco-caprylate/caprate, C12-15 alcohols benzoate and octyldodecyl stearoyl stearate. The silicone components comprise dimethicone and trimethylsiloxysilicate. Thus, in a preferred embodiment, the components of the oil binder constituent of the frost pressed powder composition are identical to the components utilized in providing the oil binder constituent of the cream pressed powder composition.

In the preferred embodiment wherein these preferred esters and silicones are utilized as the oil binder constituent, coco-caprylate/caprate is present in an amount of between about 1% and about 10%, C12-15 alcohols benzoate comprises between about 1% and about 5% and octyldodecyl stearoyl stearate is about 0.25% to about 5.0% of the frost pressed powder composition. In that same preferred embodiment the silicone constituent, a mixture of dimethicone and trimethylsiloxysilicate, is present in a concentration of between about 1% and about 10% of the frost pressed powder composition.

In a more preferred embodiment, the oil binder constituent includes coco-caprylate/caprate, present in an amount of between about 4% and about 8%. The C12-15 alcohols benzoate component is present in an amount of between about 1.5% and about 3.5% and the octyldodecyl stearoyl stearate constitutes between about 0.5% and about 1.5% of the composition. The mixture of dimethicone and trimethylsiloxysilicate, the silicone component, is present in an amount of between about 2.5% and about 7.5% of the frost pressed powder composition.

A final preferred constituent of the frost pressed powder composition is the preservative constituent. The preservative constituent of the frost pressed powder composition serves the same function as in the cream pressed powder composition, to wit, the preservation of the cosmetic composition between formulation and use.

In the preferred embodiment wherein a preservative component is included, the preservative component is preferably present in an amount of between about 0.25% and about 2%, more preferably, between about 0.5% and about 1.5%.

In a particularly preferred embodiment, the preservative constituent is provided by methylparaben, ethylparaben, propylparaben and imidazolidinyl urea. These constituents, in this particularly preferred embodiment, are present in an amount such that the methyparaben, ethylparaben and propylparaben together comprise between about 0.1% to about 1% of the frost pressed powder composition. The imidazolidinyl urea, preferably present in the frost pressed powder as imidazolidinyl urea coated talc, is similarly present in an amount of between about 0.1% and about 1% by weight.

More preferably, the mixture of methylparaben, ethylparaben and propylparaben constitutes between about 0.2% and about 0.8% of the frost pressed powder composition whereas the imidazolidinyl urea coated talc is representative of between about 0.4% and about 0.8% of this composition.

The following examples are given to illustrate the present invention. Because these examples are given for illustrative purposes only, the subject invention should not be deemed limited thereto.

EXAMPLE 1

Preparation of a Cream Powder Eyes Composition

A first mixing container was charged with 35.25 parts lecithin coated talc, 14 parts lecithin coated iron oxides, 2 parts polyethlene, 5 parts zinc stearate, 30 parts lecithin coated mica, 4 parts bismuth oxychloride, 0.2 part methylparaben, 0.15 part ethylparaben, 0.1 part propylparaben and 0.3 part imidazolidinyl urea, all parts reported being by weight. The above solid constituent were pulverized so that the resultant solid mixture passed though an 0.01 inch screen.

A second mixing container, provided with mixing and heating means, was separately charged with 2.25 parts cococaprylate/caprate, 1.25 parts C12-15 alcohols benzoate and 0.5 part octyldodecyl stearoyl stearate. After charging these oil phase constituents into the second mixing container the ingredients were mixed while being heated at a temperature of 70° C. Upon obtaining a homogenous mixture, 5 parts of a mixture of dimethicone and trimethylsiloxysilicate was added to the liquid, at 70° C., and mixing was continued until the silicone component was completely blended into the mixture.

The uniform oil mixture in the second container was transferred into the first mixing container accompanied by intense mixing. Mixing continued until a homogeneous blend was obtained. Upon obtaining the desired color shade the product, a cream powder eyeshadow composition, was discharged from the container.

EXAMPLE 2

Preparation of a Frost Powder Eyeshadow Composition

A first mixing container was charged with 17 parts by weight, hereinafter denoted as parts, lecithin coated talc, 12 parts lecithin coated mica, 5 parts zinc stearate, 2 parts polyethylene, 0.2 part methylparaben, 0.15 part ethylparaben, 0.1 part propylparaben, 0.3 part imidazolidinyl urea, 0.5 part lecithin coated chromium oxide greens, 7.5 parts talc, 5 parts bismuth oxychloride on mica and 10 parts bismuth oxychloride. These solid ingredients were mixed and pulverized until a uniform mixture that passed through an 0.01 inch screen was obtained. The pulverized solid mixture was thereupon transferred into a second, larger capacity, mixing container.

The second container into which the pulverized powder introduced was further charged with 25.75 parts of chromium oxide greens coated on titanated mica. This pearlescent colorant was blended with the pulverized powder at a temperature of up to 65° C. until a uniform mixture was obtained.

A third mixing container was charged with 6 parts coco-caprylate/caprate, 2.5 parts C12-15 alcohols benzoate and 1 part octyldodecyl stearoyl stearate. These ingredients were mixed until a uniform liquid mixture was obtained. Thereupon, with mixing continued, 5 parts of a silicone mixture of dimethicone and trimethylsiloxysilicate was introduced therein while the contents of the container were maintained at 70° C. Mixing and heating at 70° C. continued until a uniform liquid mixture was obtained.

The liquid mixture, an oil phase mixture, was next transferred into the second mixing container containing the earlier described solid mixture. Upon transferral of the liquid mixture into the second mixing container mixing was initiated. This mixing continued until a homogenous blend was obtained. After minor additions of colorants to meet the desired color standard, the mixture in the second container, a frost powder eyeshadow composition, was removed therefrom.

EXAMPLE 3

Preparation of an Eyeshadow Product

Equal volume amounts of the cream eyeshadow powder composition, produced in accordance with Example 1, and the frost eyeshadow powder composition, produced in accordance with Example 2, were disposed adjacent to each other in a single pan. The two compositions in the single pan were pressed at the same pressure to obtain two solidified compositions disposed adjacent to each other. The two pressed eyeshadow compositions meeting all aesthetic and cosmetic requirements, were thus formed in a single pan.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A pressed powder cosmetic product comprising at least one cream pressed powder composition and at least one frost pressed powder composition, each of which comprise at least one filler, a portion of which is coated with a surfactant; at least one colorant a portion of which is coated with a surfactant, and a powder binder comprising at least 2% of a first component selected from the group consisting of polyethylene, boron nitride, polymethacrylate, and mixtures thereof, and at least 1% of a second component selected from the group consisting of zinc stearate, calcium stearate, lithium stearate, magnesium stearate, lauroyl lysine, calcium silicate, or mixtures thereof wherein said powder binder is present in a concentration of between about 0.5% and about 15% by weight of the cream pressed powder and about 3% and about 15% of the frost pressed powder; and an oil binder comprising esters and silicones; and wherein said frost pressed powder composition comprises a pearlescent powder; whereby said powder compositions are disposed adjacent to each other in a single pan thereby forming a unitary solid.

2. A product in accordance with claim 1 wherein said surfactant used to coat said filler and said colorant is selected from the group consisting of lecithin, egg oil, egg yolk extract, animal collagen, animal elastin, amino acids and mixtures thereof.

3. A product in accordance with claim 2 wherein said filler is selected from the group consisting of talc, mica, bentonite, bismuth oxychloride, calcium silicate, calcium carbonate, nylon, polyvinylidene copolymers, isopropyl triisostearyl titanate, corn starch, kaolin and mixtures thereof.

4. A product in accordance with claim 3 wherein said colorant is selected from the group consisting of titanium dioxide titanated mica, iron oxides, carmine, chromium hydroxide green, chromium oxide greens, ferric ammonium ferrocyanide, ferric ferrocyanide, manganese violet, ultramarine violet, ultramarine blue, ultramarine red, ultramarine pink, D&C Red No. 6 barium/strontium lake, D&C Red No. 7 calcium lake, D&C Red No. 27 aluminum lake, D&C Red No. 30 lake, D&C Yellow No. 5 aluminum lake, D&C Yellow No. 6 aluminum lake and mixtures thereof.

5. A product in accordance with claim 4 wherein said cream pressed powder composition and said frost pressed powder composition include a preservative constituent.

6. A product in accordance with claim 5 wherein said preservative constituent is selected from the group consisting of methylparaben, ethylparaben, propylparaben, imidazolidinyl urea and mixtures thereof.

7. A pressed powder cosmetic product comprising a cream pressed powder composition and a frost pressed powder composition disposed adjacent to each other in a single pan, said cream pressed powder composition comprising:
(a) at least one surfactant coated filler;
(b) at least one surfactant coated colorant;
(c) a powder binder comprising a first component selected from the group consisting of polyethylene, boron nitride, polymethylmethacrylate and mixtures thereof and a second component selected from the group consisting of zinc stearate, calcium stearate, lithium stearate, magnesium stearate, calcium silicate, kaolin, lauroyl lysine and mixtures thereof and;
(d) at least one liquid binder constituent; and said frost pressed powder composition comprising:
(a) at least one surfactant coated filler;
(b) at least one surfactant coated colorant;
(c) at least one pearlescent colorant;
(d) at least one uncoated filler;
(e) a powder binder comprising a first component selected from the group consisting of polyethylene, boron nitride, polymethylmethacrylate and mixtures thereof and a second component selected from the group consisting of zinc stearate, calcium stearate, lithium stearate, magnesium stearate, calcium stearate, kaolin, lauroyl lysine and mixtures thereof; and
(f) at least one liquid binder.

8. A product in accordance with claim 7 wherein said components of said cream pressed powder composition are present in said composition in amounts as follows:
(a) between about 30% and about 90%;
(b) between about 0.1% and about 40%;
(c) between about 0.5% and about 15%; and
(d) between 1% and about 20%; and
said components of said frost pressed powder composition are present in said composition in amounts as follows:
(a) between about 15% and about 50%;
(b) between about 0.1% and about 40%
(c) between about 20% and about 60%;
(d) between about 0% and about 15%;
(e) between about 3% and about 15%; and
(f) between about 7% and about 22%,
all said percentages being by weight based on the total weight of the composition.

9. A product in accordance with claim 8 wherein said concentration of said constituents of said cream pressed powder composition are:

(a) between about 50% and about 75%;
(b) between about 1% and about 30%;
(c) between about 1% and about 7%; and
(d) between about 5% and about 13%; and
wherein said concentration of said constituents of said frost pressed powder composition are:
(a) between about 20% and about 35%;
(b) between about 1% and about 10%;
(c) between about 25% and about 40:
(d) between about 1% and about 10%;
(e) between about 5% and about 15%; and
(f) between about 10% and about 20%.

10. A product in accordance with claim 8 wherein said surfactant coating of said fillers and said colorants of said cream pressed powder composition and said frost pressed powder composition is lecithin.

11. A product in accordance with claim 10 wherein said first powder binder component of said cream pressed powder composition and said frost pressed powder composition is polyethylene and said second powder binder component of said cream pressed powder composition and said frost pressed powder composition is zinc stearate.

12. A product in accordance with claim 11 wherein said first powder binder component is present in a concentration of between about 2% and about 5% in both said cream pressed powder and said frost pressed powder compositions and said second powder binder component is present in a concentration of between about 1% and about 5% and between about 1% and about 10%, respectively, in said cream pressed powder composition and said frost pressed powder composition.

13. A product in accordance with claim 11 wherein said coated filler constituent of both said cream pressed powder composition and said frost pressed powder composition is selected from the group consisting of talc, mica and mixtures thereof.

14. A product in accordance with claim 12 wherein said liquid binder constituent of said cream pressed powder composition and said frost pressed powder composition both are selected from the group consisting of coco-caprylate/caprate, C12-15 alcohols benzoate, octyldodecyl stearoyl stearate, dimethicone, trimethylsiloxysilicate and mixtures thereof.

15. A product in accordance with claim 18 wherein said cream pressed powder composition and said frost pressed powder composition both comprises a preservative component present in a concentration of between about 0.25% and about 2%.

16. An eyeshadow comprising the cosmetic product of claim 1.

17. A blusher comprising the cosmetic product of claim 1.

18. An eyeshadow comprising the cosmetic product of claim 12.

19. A blusher comprising the cosmetic product of claim 12.

* * * * *